United States Patent [19]

Puskas

[11] 4,034,052

[45] July 5, 1977

[54] ALKENYLATION CATALYSTS

[75] Inventor: Imre Puskas, Glen Ellyn, Ill.

[73] Assignee: Standard Oil Company (Indiana), Chicago, Ill.

[22] Filed: Sept. 29, 1975

[21] Appl. No.: 617,368

[52] U.S. Cl. .......................................... 260/671 C
[51] Int. Cl.² ........................................ C07C 3/00
[58] Field of Search .................... 260/671 A, 671 C

[56] References Cited

UNITED STATES PATENTS

| | | | |
|---|---|---|---|
| 1,934,123 | 11/1933 | Hofmann et al. | 260/671 A |
| 2,994,725 | 8/1961 | Shaw et al. | 260/671 C |
| 3,028,441 | 4/1962 | Bush et al. | 260/671 C |
| 3,244,758 | 4/1966 | Eberhardt | 260/671 R |
| 3,766,288 | 10/1973 | Shima et al. | 260/671 A |

FOREIGN PATENTS OR APPLICATIONS 50-25530  3/1975  Japan

Primary Examiner—O. R. Vertiz
Assistant Examiner—Wayne A. Langel
Attorney, Agent, or Firm—Geoffrey M. Novelli; Arthur G. Gilkes; William T. McClain

[57] ABSTRACT

Unsaturated amines, primary and secondary saturated amines, N,N,N',N'-tetramethylethylenediamine, N,N,N',N'-tetramethyl-1,3-propanediamine, and ammonia cocatalysis with alkali metals for alkenylation of alkylaromatics having benzylic hydrogen with conjugated diolefins of 4–15 carbon atoms. Improved trans:-cis product ratio and improved yield are produced by these nitrogen containing cocatalysts.

19 Claims, 3 Drawing Figures

| CATALYST | POTASSIUM | POTASSIUM-MORPHOLINE |
|---|---|---|
| BUTADIENE TO O-XYLENE MOLAR RATIO: | 0.022 | 0.019 |
| TRANS TO CIS 5-OTP RATIO: | 1.27 | 3.13 |

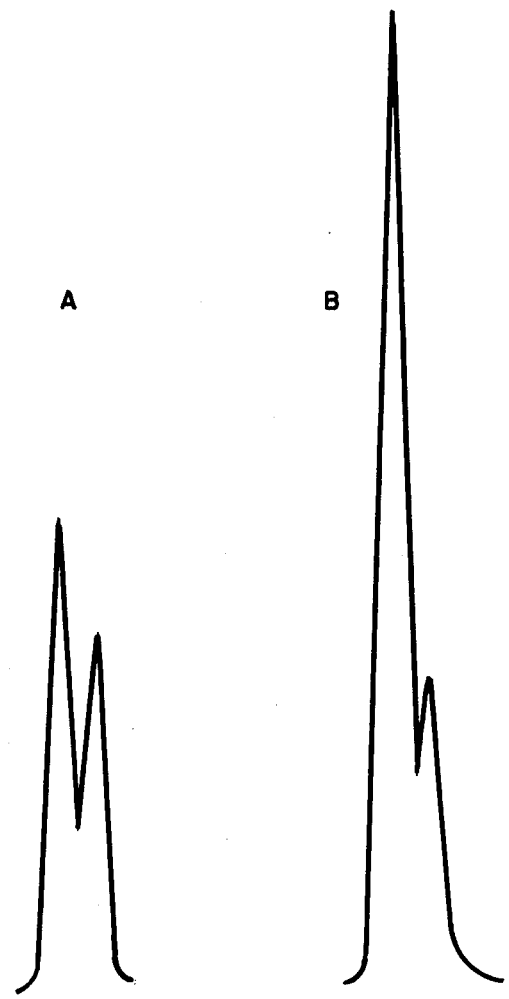

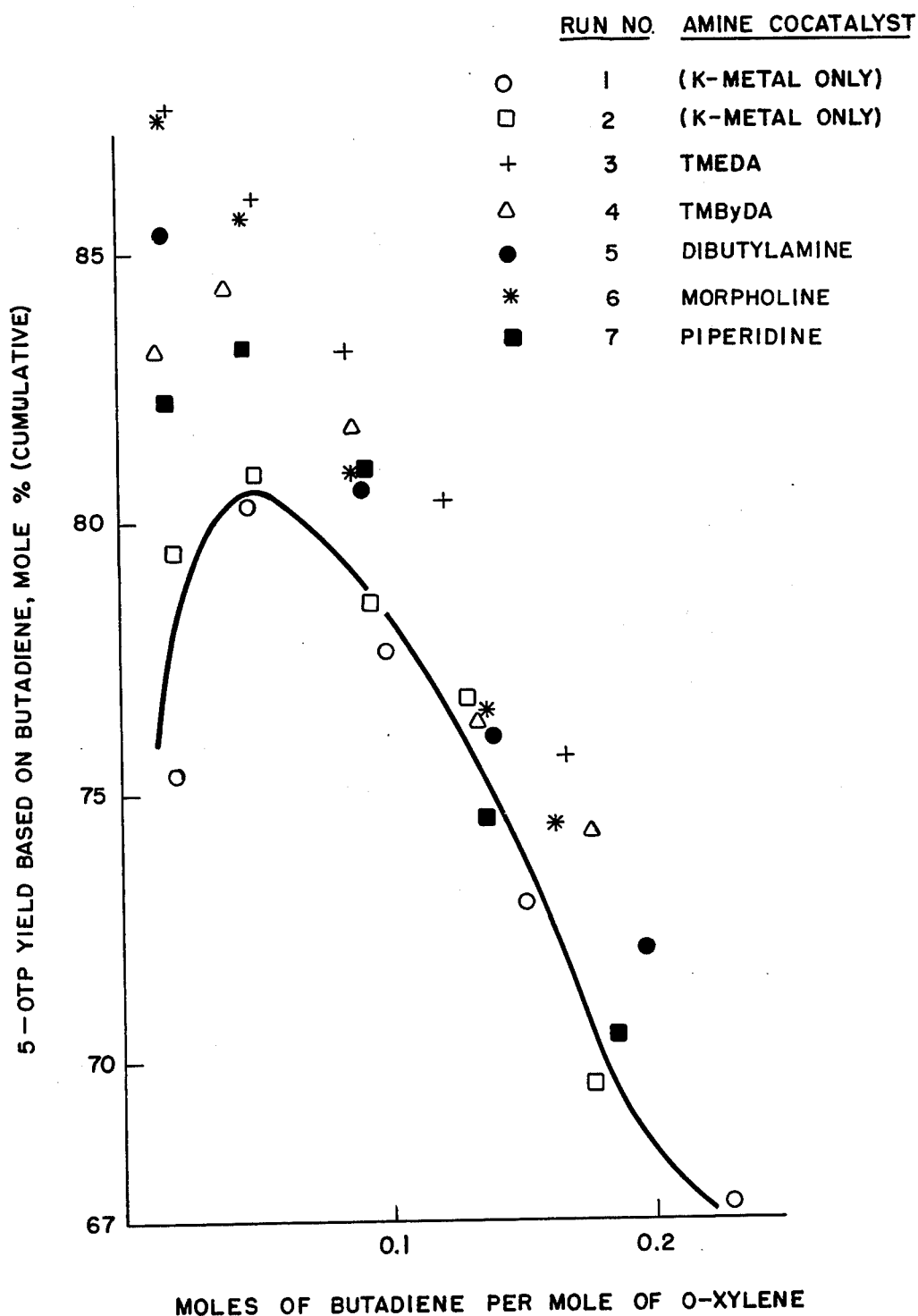

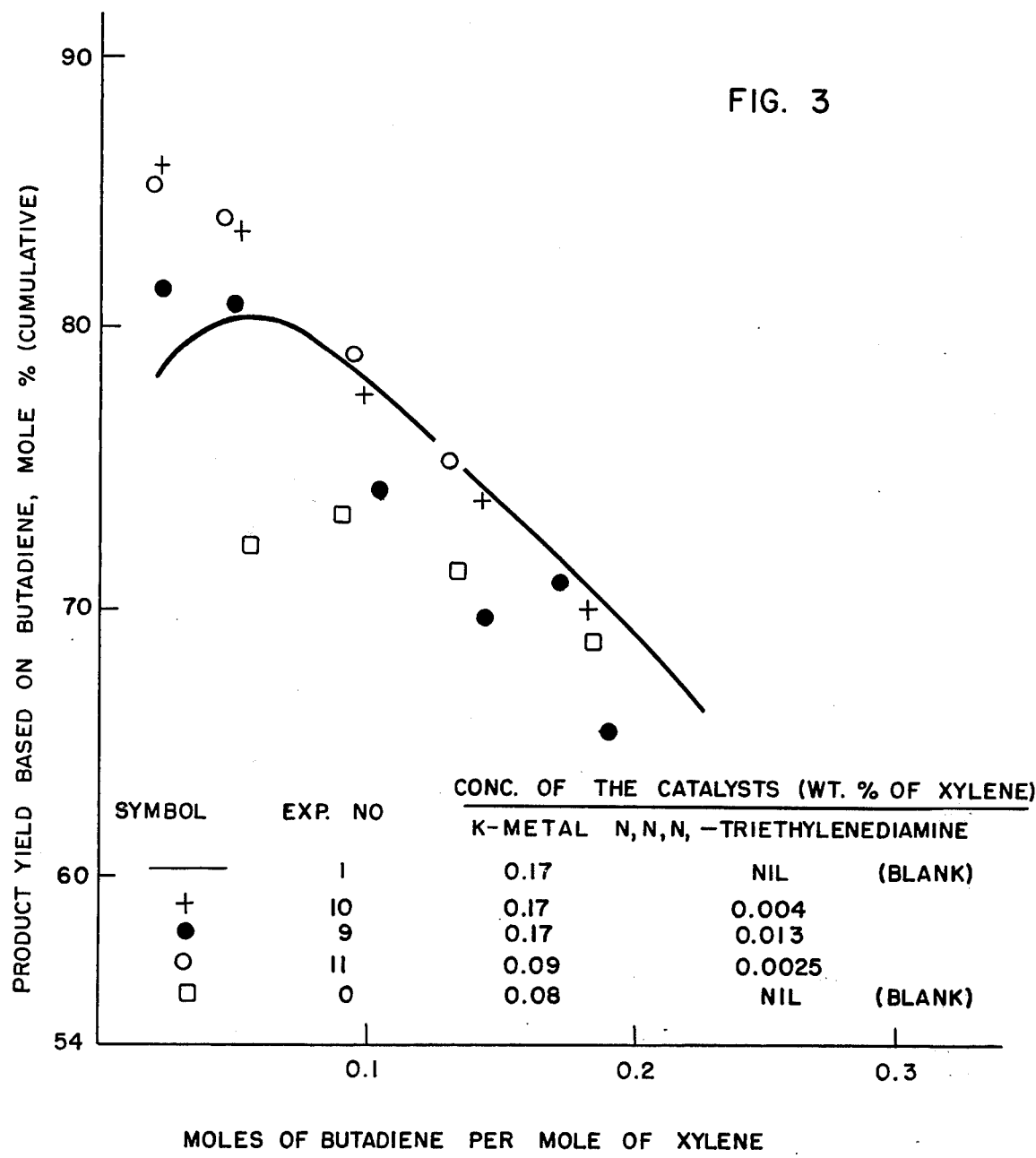

ALKENYLATION CATALYSTS

BACKGROUND

Alkali metal and alkali metal alloy catalysts have been used to catalyze these alkenylation reactions as taught in Eberhardt, U.S. Pat. No. 3,244,758 (1966), Shima et al. U.S. Pat. Nos. 3,766,288 (1973) and U.S. Pat. 1,934,123 (1928) which are all specifically incorporated herein by reference. Use of amine co-catalyst in these alkenylation reactions according to this invention can alter the isomeric product distribution and yield better selectivity to the desired product.

Certain tertiary amines are known to increase the reactivity of organolithium and organosodium catalysts according to *Polyamine-Chelated Alkali Metal Compounds*. Ed. A. W. Langer. Advances in Chemistry Series No 130. American Chemical Society, 1974. However, the amines herein described are ineffective as cocatalysts with lithium or sodium alone for these alkenylation reactions.

SUMMARY

This invention is a process for using amines or ammonia to cocatalyze alkenylation of alkylaromatics with conjugated diolefins. Representative is the amine cocatalysis of butadiene addition to o-xylene to produce 5-(o-tolyl)-pentene-2 (5-OTP); this product can undergo further reactions of ring closure, dehydrogenation and isomerization to yield isomers of dimethylnaphthalene (DMN) such as 2,6-DMN which can be oxidized and esterified to high performance polyesters.

BRIEF DESCRIPTION OF THE DRAWING

FIG. 1 is a representative gas chromatographic comparison of the trans:cis product ratio obtained with potassium alone and with an amine cocatalyst.

FIG. 2 is a plot showing the product yields during batch alkenylations of o-xylene with butadiene using various amine cocatalysts.

FIG. 3 is a plot showing the effect of various levels of initial concentration of an amine cocatalyst.

DETAILED DESCRIPTION

Amines can act as cocatalysts in combination with potassium, rubidium, cesium, alloys of these metals with each other or with other alkali metals for alkenylation reactions of this type. Conjugated diolefins of from 4 to about 15 carbon atoms can be used to alkenylate alkylaromatics having benzylic hydrogen with one or more rings. Typically butadiene is used to add to the benzylic carbon of ortho, meta, or para xylene, toluene, ethylbenzene, or any of the alkylnaphthalenes or alkylphenanthrenes to yield aromatics having a side chain containing unsaturation.

Useful amines of 1-60 carbon atoms for cocatalysts with the alkali metals and alloys are unsaturated amines, primary and secondary saturated amines, ammonia, N,N,N',N'-tetramethylethylenediamine, and N,N,N',N'-tetramethyl-1,3-propanediamine.

Sterically hindered amines such as dicyclohexylamine are indifferent and ineffective in these reactions as are most saturated tertiary amines, such as N,N'-dimethyl piperazine, 1,4-diazabicyclo-[2,2,2]-octane, N,N,N',N'-tetramethyl-1,4-butanediamine and the acidic aromatic amines such as carbazole.

Useful unsaturated amines include dimethyl vinylamine, dimethyl allylamine, methyl ethyl allylamine, methyl butyl vinylamine, 1-dimethylamino-2-propyne, N.N,N',N'-tetramethyl-2-butyne-1,4-diamine, N,N,N',N'-tetramethyl-2-butene-1,4-diamine, tributenylamine, methylethylbutenylamine, N-butenylmorpholine, butenylamine, allyl amine, 3-amino propyne-1, aniline, oleylamine (1-amino-octadecene-9), o-toluidine, 1aminocyclohexene, m-toluidine, p-toluidine, amino pyridine isomers, xylidine isomers, amino quinoline isomers, N-vinyl piperidine, N-methylamino pyridine isomers, N-vinyl coniine, N-ethylamino pyridine isomers, N-vinylmorpholine, N-methyl aminoquinoline isomers, N,N'-divinylpiperazine, methyl allylamine, methyl benzylamine, ethyl allylamine, ethyl benzylamine, methyl propargyl amine, ethyl propargylamine, methyl cyclohexenylamine, butyl cyclohexenyl amine, N-methylaniline, N-ethylaniline, N-propylaniline, N-methyltoluidines (o, m, p-isomers), N-methylnaphthylamines (alpha and beta isomers).

Useful saturated primary amines include methylamine, ethylamine, propylamine, isopropylamine, n-butylamine, 2-aminobutane, isobutylamine, n-amylamine, 2-amino pentane, 3-amino pentane, 1-amino-3-methylbutane, n-hexylamine, dodecylamine, hexadecylamine, ethylenediamine, 1,3-diaminopropane, 1,4-diaminobutane, 1,5-diaminopentane, 1,6-diaminohexane, cyclohexylamine, 1,2-diaminocyclohexane and 1-adamantylamine.

Useful saturated secondary amines include dimethylamine, diethylamine, di-n-propylamine, di-n-butylamine, di-n-amylamine, di-n-octylamine, di-n-dodecylamine, di-isopropylamine, methyl ethylamine, methyl propylamine, methyl n-butylamine, methyl isobutylamine, ethyl butylamine, ethyl hexylamine, ethyl dodecylamine, N,N'-dimethyl diamino ethane, N,N'-dimethyl-1,3-diamino propane, N,N'-diethyl-1,3-diaminopropane, N,N,N'-triethyl-1,3-diaminopropane, N-methylcyclohexylamine, N-ethylcyclohexylamine, N-ethyladamantylamine, pyrrolidine, etc.

As Table I indicates, in runs 9–11, too high a concentration of the amine can adversely affect the yield of the desired alkenylation product during alkenylation. While generally the amine concentration should be within 0.0005–1.0, weight percent range based on the alkylaromatic reactant, the preferred concentration range is 0.004–0.1%.

TABLE I

THE EFFECT OF AMINES ON POTASSIUM CATALYST[a]
COMPARISON OF THE 5-OTP CUMULATIVE YIELDS AND TRANS:CIS RATIOS

For each successive sample of the batch reaction products, the first sub-column is the butadiene:O-xylene molar ratio; the second sub-column is the yield in mole % based on butadiene introduced; the third sub-column in brackets is the trans:cis 5-OTP ratio.

| Run No. | Amine and its initial concentration (Wt. % of Xylene) | Sampling 1 | 2 | 3 | 4 | 5 |
|---|---|---|---|---|---|---|
| 1 | nil | 0.022 75.4 (1.27) | 0.050 80.4 (1.33) | 0.101 77.6 (1.36) | 0.152 72.9 (1.38) | 0.229 69.3 (1.41) |
| 2 | nil | 0.021 79.5 (1.24) | 0.052 80.9 (1.32) | 0.095 78.5 (1.35) | 0.131 76.8 (1.38) | 0.175 69.6 (1.40) |
| 3 | 0.040% TMEDA[b] | 0.021 0.75 (1.95) | 0.052 86.0 (1.98) | 0.087 83.1 (1.88) | 0.122 80.2 (1.79) | 0.166 75.6 (1.78) |
| 4 | 0.024% TMByDA[c] | 0.018 83.1 (4.37) | 0.042 84.3 (2.68) | 0.088 81.6 (2.27) | 0.134 76.2 (2.04) | 0.176 74.1 (2.00) |
| 5 | 0.004% Dibutylamine | 0.019 85.4 (1.38) | 0.048 85.6 (1.42) | 0.091 80.7 (1.46) | 0.138 76.0 (1.49) | 0.197 72.0 (1.57) |
| 6 | 0.010% Morpholine | 0.019 87.5 (3.13) | 0.047 85.6 (2.89) | 0.089 80.9 (2.63) | 0.136 76.4 (2.42) | 0.163 74.3 (2.22) |

TABLE I-continued

THE EFFECT OF AMINES ON POTASSIUM CATALYST*
COMPARISON OF THE 5-OTP CUMULATIVE YIELDS AND TRANS:CIS RATIOS
For each successive sample of the batch reaction products, the first sub-column is the butadiene:O-xylene molar ratio; the second sub-column is the yield in mole % based on butadiene introduced; the third sub-column in brackets is the trans:cis 5-OTP ratio.

| Run No. | Amine and its initial concentration (Wt. % of Xylene) | Sampling 1 | 2 | 3 | 4 | 5 |
|---|---|---|---|---|---|---|
| 7 | 0.014% Piperidine | 0.020 82.3 (2.69) | 0.049 83.3 (2.44) | 0.091 80.9 (2.20) | 0.136 74.4 (2.08) | 0.182 70.5 (1.97) |
| 8 | 0.040% Dibutylamine | 0.019 87.0 (2.70) | 0.042 83.4 (2.81) | 0.079 76.1 (2.67) | 0.123 73.6 (2.73) | 0.167 71.6 (2.67) |
| 9 | 0.013% TEEDA$^d$ | 0.024 81.6 (4.65) | 0.052 80.9 (4.60) | 0.105 74.2 (3.70) | 0.144 69.6 (3.37) | 0.192 65.5 (2.99) |
| 10 | 0.004% TEEDA$^d$ | 0.022 86.0 (3.16) | 0.053 83.5 (3.09) | 0.098 77.7 (2.77) | 0.143 73.9 (2.51) | 0.181 69.9 (2.23) |
| 11 | 0.003% TEEDA$^d$ | 0.021 85.4 (2.36) | 0.048 84.2 (2.31) | 0.093 79.1 (2.34) | 0.132 75.3 (2.36) | 0.173 71.0 (2.36) |
| 12 | 0.008% 1,2-Diaminocyclohexane | 0.021 66.7 (3.54) | 0.048 77.6 (2.39) | 0.095 76.0 (1.83) | 0.137 73.1 (1.73) | 0.188 68.8 (1.62) |
| 13 | 0.025% 1,3-Diaminopropane | 0.025 0.5 — | 0.052 8.8 (5.65) | 0.099 43.0 (3.16) | 0.146 55.0 (2.35) | 0.181 55.8 (2.08) |
| 14 | 0.088% DABCO$^e$ | 0.021 72.6 (1.37) | 0.051 78.9 (1.37) | 0.103 76.8 (1.39) | 0.162 73.7 (1.42) | 0.216 69.1 (1.42) |
| 15 | 0.033% N,N'-Dimethylpiperazine | 0.024 74.2 (1.40) | 0.064 74.3 (1.40) | 0.110 73.7 (1.38) | 0.152 72.9 (1.44) | 0.195 69.4 (1.45) |
| 16 | 0.016% TMBDA$^f$ | 0.020 82.3 (1.23) | 0.048 82.9 (1.28) | 0.090 77.9 (1.37) | 0.138 73.8 (1.39) | 0.184 69.4 (1.43) |
| 17 | 0.014% Dicyclohexylamine | 0.019 81.7 (1.28) | 0.046 82.3 (1.31) | 0.091 77.7 (1.35) | 0.138 73.1 (1.42) | 0.187 69.1 (1.48) |
| 18 | 0.015% Carbazole | 0.021 51.9 (1.20) | 0.046 57.7 (1.23) | 0.088 66.1 (1.30) | 0.128 63.7 (1.29) | 0.170 65.8 (1.37) |

*The potassium concentration was 0.17% in all runs except No. 11, 0.09%.
$^b$TMEDA = N,N,N',N'-Tetramethylethylenediamine.
$^c$TMByDA = N,N,N',N'-Tetramethyl-2-butyne-1,4-diamine.
$^d$TEEDA = N,N,N'-Triethylethylenediamine.
$^e$DABCO = 1,4-Diazabicyclo-[2,2,2]-octane.
$^f$TMBDA = N,N,N',N'-Tetramethyl-1,4-butanediamine.

Table I shows the results of batch reactions of 1,3 butadiene alkenlation of o-xylene wherein different amines were used for co-catalysis with potassium metal. The amines in Runs 3–13 show a marked improvement over runs 1 and 2, using potassium alone, in the production of the preferred trans isomer of 5-o tolyl pentene-2 (5-OTP) product as depicted in FIG. I. The trans isomer is more selective than the cis isomer in the subsequent cyclization of 5-OTP to yield substituted tetralin. In addition, the yield of 5-OTP product is generally improved in runs 3–13 over potassium alone, although runs 12 and 13 show poor yield due to excessively high initial concentration of these primary amines.

The following examples do not indicate any limitation upon the scope of the claims.

EXAMPLE I

The apparatus used was a 2 liter resin kettle equipped with a mechanical stirrer (air driven), baffles, thermometer, inlet and outlet for dry nitrogen purge and a glass dispersion tube for the introduction of the butadiene. The apparatus was heated with a silicon oil bath. The temperature was manually controlled within ±2° C. About 1250 g of o-xylene was charged into the dry apparatus and with slow stirring heated to 140°–144° C under dry nitrogen purge to remove the residual moisture content by azeotropic distillation. The mixture was then cooled to 120° C and about 10 grams of tetradecane, weighed with milligram accuracy, was added to serve as a gas-chromatographic standard. Based on the weight of xylene 0.17% potassium metal and 0.010% morpholine were charged and dispersed in the system by agitation. The agitation rate was usually in the 1200–1600 rpm range. The reactions were conducted at 110–114° C unless otherwise specified. The butadiene controlled rate of about 100 ccm per minute into the reaction kettle. After the start of the butadiene flow, there was an induction period ranging from 2 to 60 minutes, depending on the catalyst and the purity of the reagents. With potassium metal and "pure" reagents the induction period was only 2–5 minutes. Then color development indicated the start of the reaction, the color gradually deepening to dark black. During the reaction, samples were periodically withdrawn from the reaction mixture (quenched simply by shaking) for a quantitative determination of the products by gas chromatography. At the times of the samplings, the weights of the consumed butadiene were also determined by disconnecting and weighing the butadiene reservoir.

EXAMPLE II

Using the equipment and procedure described in Example I a run was made using an alloy of 0.1% sodium and 0.1% potassium based on the weight of the xylene and another run with the same alloy was made adding 0.09% TMEDA. Both runs were made using butadiene having 155 ppm water which decreased activity but the effect of the amine cocatalyst is indicated by a trans:cis ratio 2.11 compared to 1.35 for the alloy alone, and by cumulative yield of 59.7% 5-OTP compared to 40% for the alloy alone. Other examples are listed in Table I.

FIGS. 2 and 3 were plotted as follows: the yield of the isomeric 5-(o-tolyl)-pentenes was plotted as the function of the butadiene introduced, this latter quantity being expressed in the units of butadiene to o-xylene molar ratio. The calculation of the yield was based on the butadiene used. (Since more butadiene molecules were lost to by-products than o-xylene molecules, the yield values calculated on the o-xylene consumption would be substantially higher). Every data point represents the cumulative mole % yield from the start of the reaction.

I claim:

1. In a process for alkenylation of alkylaromatics having benzylic hydrogen with conjugated diolefins of 4–15 carbon atoms in the presence of an alkali metal selected from the group consisting of potassium, rubidium, cesium, and alloys of said metals with each other or with other alkali metals, the improvement comprising carrying out the process in the presence of a cocatalyst selected from the group consisting of unsaturated amines having 1–60 carbon atoms, primary and secondary saturated amines having 1–60 carbon atoms, N,N,N',N'-tetramethylethylenediamine, N,N,N'N'-tetramethyl-1,3-propanediamine, and ammonia.

2. The process of claim 1 wherein the alkylaromatic is O-xylene, the diolefin is 1,3-butadiene, and the alkali metal is potassium.

3. The process of claim 2 wherein the cocatalyst is N,N,N′N′-tetramethyl-2-butyne-1,4-diamine.

4. The process of claim 2 wherein the cocatalyst is N,N,N′,N′-tetramethylethylenediamine.

5. The process of claim 2 wherein the cocatalyst is dibutylamine.

6. The process of claim 2 wherein the cocatalyst is morpholine.

7. The process of claim 2 wherein the cocatalyst is piperidine.

8. The process of claim 2 wherein the cocatalyst is N,N,N′-triethylethylenediamine.

9. The process of claim 2 wherein the cocatalyst is 1,2-diaminocyclohexane.

10. The process of claim 2 wherein the cocatalyst is 1,3-diaminopropane,

11. The process of claim 1 wherein the cocatalyst is present in an amount 0.0005–1.0% of the alkylaromatic reactant by weight.

12. The process of claim 11 wherein the alkali metal is potassium.

13. The process of claim 11 wherein the alloy is a sodium-potassium alloy.

14. The process of claim 1 wherein the cocatalyst is an unsaturated amine.

15. The process of claim 1 wherein the cocatalyst is a primary or secondary saturated amine.

16. The process of claim 1 wherein the cocatalyst is N,N,N′,N′-tetramethylethylenediamine.

17. The process of claim 1 wherein the cocatalyst is N,N,N′,N′-tetramethyl-1,3-propanediamine.

18. The process of claim 1 wherein the cocatalyst is ammonia.

19. The process of claim 1 wherein the alkylaromatic is O-xylene, the diolefin is 1,3-butadiene, and the alloy is a sodium-potassium alloy.

* * * * *

UNITED STATES PATENT OFFICE
CERTIFICATE OF CORRECTION

Patent No. 4,034,052　　　　　　　　　　　Dated　July 5, 1977

Inventor(s)　Imre Puskas

It is certified that error appears in the above-identified patent and that said Letters Patent are hereby corrected as shown below:

Column 2, line 18, "laminocyclohexene" should be
-- 1-aminocyclohexene --;
" 2, " 23, "N,N'-divinylpiperazine, methyl" should be
-- N,N'-divinylpiperazine methyl --

Signed and Sealed this

*Twenty-second* Day of *November 1977*

[SEAL]

*Attest:*

RUTH C. MASON　　　　　LUTRELLE F. PARKER
*Attesting Officer*　　　*Acting Commissioner of Patents and Trademarks*